United States Patent [19]

Zimmer et al.

[11] Patent Number: 6,022,895
[45] Date of Patent: *Feb. 8, 2000

[54] SUBSTITUTED AMINO COMPOUNDS AND THEIR USE AS SUBSTANCES HAVING AN ANALGESIC EFFECT

[75] Inventors: Oswald Zimmer; Wolfgang Werner Alfred Strassburger, both of Wuerselen; Helmut Heinrich Buschmann, Aachen; Werner Englberger; Elmar Josef Friderichs, both of Stolberg, all of Germany

[73] Assignee: Gruenenthal GmbH, Aachen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/038,033

[22] Filed: Mar. 11, 1998

[30] Foreign Application Priority Data

Mar. 14, 1997 [DE] Germany ............... 197 10 628

[51] Int. Cl.[7] .................. A61K 31/135; C07C 211/21
[52] U.S. Cl. .................. 514/548; 514/247; 514/255; 514/256; 514/257; 514/299; 514/307; 514/357; 514/372; 514/374; 514/378; 514/385; 514/436; 514/438; 514/452; 514/461; 514/463; 514/469; 544/224; 544/253; 544/335; 544/336; 546/139; 546/152; 546/329; 548/146; 548/202; 548/206; 548/215; 549/20; 549/22; 549/74; 549/377; 549/462; 549/491; 564/315; 564/316; 564/320
[58] Field of Search .................. 514/648, 247, 514/255, 256, 299, 257, 307, 357, 372, 374, 378, 385, 438, 436, 452, 461, 463, 469; 564/315, 320, 316, 544/224, 253, 335, 336; 546/139, 152, 329; 548/146, 202, 206, 215; 549/20, 22, 74, 377, 462, 491

[56] References Cited

U.S. PATENT DOCUMENTS 3,489,760  1/1970  Eissler ................... 564/319

FOREIGN PATENT DOCUMENTS 623394    2/1963   Belgium .
1203247   10/1962  Germany .
1149002   5/1963   Germany .
956616    4/1964   United Kingdom .

OTHER PUBLICATIONS

Cavalla et al., "Compounds Derived from the Mannich Bases of Beta–Phenylpropiophenone" *J. Med. Chem.* 7(6):716–21 (1964).

Moffett et al., "A Mild Method For Dehydrating Some Carbinols to Alkenes. 1,1–Diarylaminolkenes as Analgesics" *Organic Preparations and Procedures Int.* 11(2):53–61 (1979).

Barron et al., "Compounds Affecting the Central Nervous System. III. Substituted 1,1–Diaryl–t–aminopropanols and Related Compounds" *J. Med. Chem.* 8(6):836–41 (1965).

Waringa et al., "1,1–diaryl–3–aminopropenes and some related compounds I" *Eur. J. Med. Chem.* 10(4):343–48 (1975).

*Chemical Abstracts* 72:54913e (1970).

Jones et al, J. Med. Chem., vol. 14, No. 2, pp. 161–164, 1971.

*Primary Examiner*—Shailendra Kumar
*Attorney, Agent, or Firm*—Evenson, McKeown, Edwards & Lenahan, P.L.L.C.

[57] ABSTRACT

Substituted amino compounds of general formula (I)

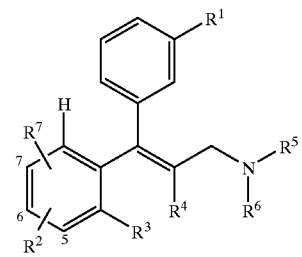

(I)

are described, as are a method of preparing them and their use as drugs, especially as analgesics.

14 Claims, No Drawings

SUBSTITUTED AMINO COMPOUNDS AND THEIR USE AS SUBSTANCES HAVING AN ANALGESIC EFFECT

This invention relates to substituted amino compounds of general formula (I)

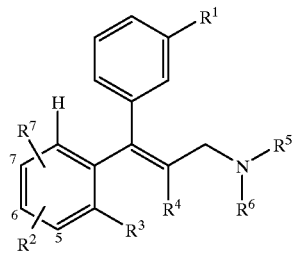

or pharmaceutically compatible salts thereof, to a method of preparing them and to their use as drugs.

Classical opioids such as morphine are very effective for the therapy of severe to very severe pain. However, their use is restricted due to their known side-effects, such as respiratory depression, vomiting, sedation and obstipation, and due to the development of tolerance. Moreover, they are less effective for neuropathic or incidental pains, from which tumor patients, amongst others, suffer in particular.

Opioids develop their analgesic effect by binding to membrane receptors which form part of the family of what are termed G protein-coupled receptors. The biochemical and pharmacological characterization of subtypes of these receptors has now given rise to the hope that subtype-specific opioids may exhibit an effect/side-effect profile which differs from that of morphine for example. Whereas morphine selectively binds to what are termed μ-receptors, endogenous enkephalins have been characterized as δ-selective peptides. In the meantime, further pharmacological investigations have indicated that several subtypes of these opioid receptors ($\mu_1, \mu_2, \kappa_1, \kappa_2, \kappa_3, \delta_1$ and $\delta_2$) probably exist.

Knowledge of the physiological importance of δ receptor-selective substances has been considerably extended due to the discovery of the non-peptidic antagonist naltrindol. Thus, it has been ascertained in the meantime that δ agonists exhibit an autonomous antinociceptive potential. In addition to a multiplicity of experimental studies on animals, an investigation has also been performed in this field using the peptidic agonist DADL on cancer patients on whom morphine no longer had an analgesic effect. When administered intrathecally, DADL exhibited an analgesic effect which was maintained for a long time.

δ agonists differ considerably from μ agonists as regards their interaction with the "endogenous opioid antagonist" cholecystokinin (CCK).

In addition to this different effect profile, it is possible that the side-effect profile of δ agonists also differs from that of μ agonists, e.g. by reduced respiratory depression.

The underlying object of the present invention was therefore to identify substances with an analgesic effect, the biological efficacy of which is partly or predominantly determined via δ opiate receptors.

It has now been found that these requirements are fulfilled by amino compounds of general formula (I).

The present invention accordingly relates to substituted amino compounds of general formula (I)

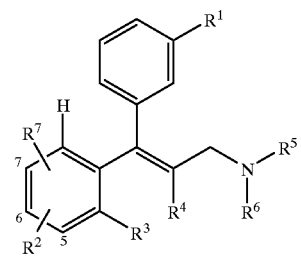

wherein $R^1$ represents H, OH, O—$C_{1-6}$-alkyl or O—$C_{3-7}$-cycloalkyl;

(wherein: $R^1$ differs from H if $R^2$ and $R^7$ are H, or an $OCH_3$ group is substituted in the 7-position);

$R^2$ represents H (if $R^1$ and $R^7$ are not both H), OH, $C_{1-6}$-alkyl, O—$C_{3-7}$-cycloalkyl, O-aryl, $C_{2-6}$-alkenyl-aryl, Cl, F, $CF_3$, $C_{1-6}$-alkoxy, aryl, heterocyclyl, $C_{1-6}$-alkyl-heterocyclyl, $C_{1-6}$-alkyl-aryl, or 5,6- or 6,7-benzo which is unsubstituted or mono- or di-substituted with Cl, F, $CF_3$, $C_{1-6}$-alkyl, O—$C_{1-6}$-alkyl or OH; (wherein: if $R^1$ is H, $R^2$ and $R^7$ cannot represent an $OCH_3$ or $CF_3$ group in the 7-position); or $R^2$ and $R^7$ together represent —O—$(CH_2)_{(1-2)}$—O— (in the 5,6- or 6,7-position);

$R^3$ represents H;

$R^4$ represents $C_{1-6}$-alkyl, or $R^3$ and $R^4$ together represent —$(CH_2)_{(1-4)}$—;

$R^5$ represents $C_{1-6}$-alkyl or $C_{3-7}$-cycloalkyl;

$R^6$ represents $C_{1-6}$-alkyl, $C_{1-6}$-alkyl-aryl, $C_{1-6}$-alkyl-heterocyclyl, —$CH_2$—CH=$C(R^8)_2$, —$CH_2$—$(C_{3-7})$-cycloalkyl or $C_{3-7}$-cycloalkyl;

$R^7$ represents H (if $R^1$ and $R^2$ are not both H), OH, $C_{1-6}$-alkyl, O—$C_{3-7}$-cycloalkyl, O-aryl, $C_{2-6}$-alkenyl-aryl, $C_{1-6}$-alkoxy, Cl, F, $CF_3$, aryl, heterocyclyl, $C_{1-6}$-alkyl-heterocyclyl, $C_{1-6}$-alkyl-aryl, or 5,6- or 6,7-benzo which is unsubstituted or mono- or di-substituted with Cl, F, $CF_3$, $C_{1-6}$-alkyl, O—$C_{1-6}$-alkyl or OH; (wherein: if $R^1$ is H, $R^2$ or $R^7$ cannot represent an $OCH_3$ or $CF_3$ group in the 7-position); and $R^8$ represents H or $CH_3$, or pharmaceutical salts thereof.

The preferred substituted amino compounds of general formula I comprise those in which $R^2$, $R^6$ and $R^7$ represent $C_{1-6}$-alkyl-aryl or $C_{1-6}$-alkyl-heterocycyl, and $R^1$, $R^3$ to $R^5$, and $R^8$ have the aforementioned meaning of general formula I, or $R^2$ and $R^7$ represent aryl or heterocyclyl, and $R^1$, $R^3$ to $R^6$, and $R^8$ have the aforementioned meaning of general formula I, or $R^1$ represents OH or —O—$C_{1-6}$-alkyl, $R^5$ and $R^6$ represent $C_{1-6}$-alkyl, and $R^2$ to $R^4$, and $R^7$, have the meaning stated in detail above.

Compounds which are particularly preferred are those in which $R^1$ represents OH, $R^5$ and $R^6$ represent methyl, and $R^2$ to $R^4$, and $R^7$, have the meaning according to general formula I.

In the present invention, the expression "$C_{1-6}$-alkyl" means straight chain or branched hydrocarbons comprising 1–6 carbon atoms. Examples which can be cited include methyl, ethyl, propyl, isopropyl, n-butyl, sec-butyl, tert-butyl, n-pentyl, neopentyl and n-hexyl.

In the context of the present invention, the expression "$C_{1-6}$-alkoxy" means straight chain or branched hydrocarbons comprising 1–6 carbon atoms, as defined above, which are bonded via the oxygen atom.

In the context of the present invention, the expression "aryl" means phenyl groups which are unsubstituted or which are singly- or multiply-substituted with OH, F, Cl, $CF_3$, $C_{1-6}$-alkyl, $C_{1-6}$-alkoxy, $C_{1-7}$-cycloalkoxy, $C_{3-7}$-cycloalkyl, $C_{2-6}$-alkylene, heterocyclyl or phenyl. The heterocyclyl or phenyl radicals may optionally be incorporated by a condensation process. This expression may optionally mean naphthyl also.

In the context of the present invention, the expression "heterocyclyl" is to be understood to mean 5- or 6-membered, saturated or unsaturated, heterocyclic compounds, on to which an aryl system is optionally condensed, and which contain 1 or 2 hetero atoms from the group comprising nitrogen, oxygen and/or sulfur.

1,4-dioxane, tetrahydrofuran and 1,4-thioxane can be cited as examples of saturated heterocyclyl groups.

Furane, thiophene, pyridine, pyrimidine, thiazole, oxazole, isooxazole, pyridazine, pyrazine, quinoline, isoquinoline, phthalazine and quinazoline can be cited as examples of unsaturated heterocyclyl groups.

In the context of the present invention, the expression "$C_{1-6}$-alkyl-aryl" or "$C_{1-6}$-alkyl-heterocyclyl" mean that the "aryls" or "heterocyclyls" as defined above are bonded via a $C_{1-6}$-alkyl group.

In the context of the present invention, the expression "silanyl compound" is to be understood to mean trialkyl or triarylsilyls, dialkylarylsilyls or diarylalkylsilyls which are used as a protective group for the hydroxy function. Examples include triethylsilyl, tripropylsilyl, dimethylphenylsilyl, di-tert-butylphenylsilyl, triisoproylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl or propyl-diphenylsilyl.

The present invention also relates to a method of preparing the substituted amino compounds of general formula (I), which is characterized by the reaction of a tertiaryalcohol of general formula (II)

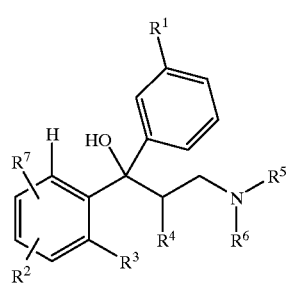

(II)

wherein $R^1$ to $R^7$ have the same meaning as in formula (I), with semi-concentrated or concentrated organic or inorganic acids, particularly formic acid or hydrochloric acid, within a temperature range from 0° C. to 100° C., wherein the tertiary alcohols of general formula (II) are obtained by reacting β-aminoketones of general formula (III)

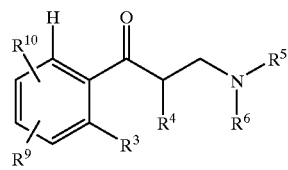

(III)

wherein $R^3$ to $R^6$ have the same meaning as in formula (I), $R^9$ is defined as $R^2$, and $R^{10}$ is defined as $R^7$, except that the hydroxy function is present in a protected form as a benzyloxy or silanyloxy group, with an organometallic compound of formula IV,

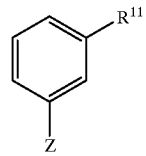

(IV)

in which Z represents MgCl, MgBr, MgI or Li, and $R^{11}$ is defined as $R^1$ except that the hydroxy function is present in a protected form as a benzyloxy or silanyloxy group, such as tert-butyldiphenylsilyloxy for example, to form a compound of formula (IIa)

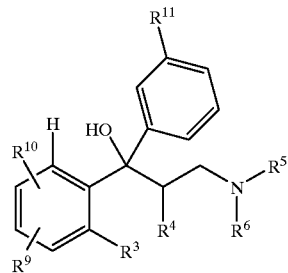

(IIa)

and the latter is then converted into the compound of formula (II).

The reaction of compounds (III) and (IV) is conducted in an aliphatic ether, for example diethyl ether and/or tetrahydrofuran, at temperatures between −70° C. and +60° C. Compounds of formula (IV) in which Z represents a lithium atom are obtained from compounds of formula (IV) in which Z represents Br or I by halogen-lithium exchange, by means of an n-butyllithium/n-hexane solution for example.

Various methods are available for the reaction of a compound of formula (IIa) to form a compound of formula (II), depending on $R^9$, $R^{10}$ and $R^{11}$, respectively.

If $R^9$, $R^{10}$ and/or $R^{11}$ represent a benzyloxy group, this reaction is advantageously effected by reductive debenzylation with catalytically activated hydrogen, wherein platinum or palladium, absorbed on a support material such as activated carbon, are employed as the catalyst. The reaction is conducted in a solvent such as acetic acid or a $C_{1-4}$-alkyl alcohol at pressures of 1 to 100 bar and temperatures of +20° C. to +100° C., wherein compound (IIa) is preferably used in the form of one of the salts thereof.

If $R^9$, $R^{10}$ and/or $R^{11}$ represent a silyl group, the protective group is split off by reacting the corresponding compound of formula (IIa), at +20° C. and in an inert solvent, such as tetrahydrofuran, dioxane or diethyl ether for example, with tetra-n-butylammonium fluoride or with a methanolic solution of hydrogen chloride.

If $R^9$, $R^{10}$ and/or $R^{11}$ represent a methoxy radical in the compound of formula (IIa), the compound of formula (II) in which $R^1$ represents a hydroxy group can be prepared by reaction with diisobutylaluminium hydride in an aromatic hydrocarbon, such as toluene or xylene, at a temperature of between 60° C. and 130° C. The analogous compound of formula (I) can also be obtained directly by heating IIa under reflux, either with a solution of hydrogen bromide in glacial acetic acid or with concentrated hydrobromic acid.

Compounds of formula I in which $R^1$, $R^2$ and/or $R^7$ represent OH can also be obtained from compounds of formula (I) in which $R^1$ and/or $R^2$ and/or $R^7$ represent a methoxy group, by reaction with diisobutylaluminium hydride as described above.

The compounds of formula (I) can be converted into their salts, in the manner known in the art, with physiologically compatible acids such as hydrochloric acid, hydrobromic acid, sulfuric acid, methanesulfonic acid, formic acid, acetic acid, oxalic acid, succinic acid, tartaric acid, mandelic acid, fumaric acid, acetic acid, citric acid, glutamic acid and/or aspartic acid. Salt formation is preferably conducted in a solvent such as diethyl ether, diisopropyl ether, an alkyl ester of acetic acid, acetone and/or 2-butanone. Trimethylchlorosilane in a solution which contains water is particularly suitable for the preparation of hydrochlorides.

The present invention further relates to the use of the substituted amino compounds of general formula (I) according to the invention as drugs. In addition to at least one compound of formula (I) according to the invention, formulations which have an analgesic effect contain adjuvant substances, for example support media, solvents, diluents, colorants and binders. The selection of these adjuvant substances and the amounts thereof which are used depend on whether the drug is to be administered orally, intravenously, intraperitoneally, intradermally, intramuscularly, intranasally, buccally or locally. Preparations in the form of tablets, chewable tablets, dragees, capsules, granules, drops, juices or syrups are suitable for oral application. Solutions, suspensions, readily reconstitutable dry preparations and sprays are suitable for parental and topical application and for application by inhalation. Compounds according to the invention in a deposit in dissolved form, in a supporting film or in a patch, optionally with the addition of agents which promote dermal penetration, are examples of suitable percutaneous forms of application. The compounds according to the invention can be released in a delayed manner from forms of preparations which can be applied orally or percutaneously. The amount of active ingredient to be administered to the patient varies depending on the weight of the patient, on the type of application, on the indication and on the degree of severity of the illness.

The following examples serve to explain the method according to the invention in greater detail.

Silica gel 60 (0.40–0.063 mm), supplied by E. Merck, Darmstadt, was used as the stationary phase for column chromatography. Thin layer chromatography investigations were performed using ready-to-use HPTLC plates of silica gel 60 F 254, supplied by E. Merck, Darmstadt. The mixture ratios of the mobile phases for all the chromatographic investigations are always given in volume/volume.

EXAMPLE 1

3-(2-dimethylaminomethyl-3,4-dihydro-naphth-1-yl)-phenol hydrochloride

1st step: (RS)-2-dimethylaminomethyl-3,4-dihydro-2H-naphthalen-1-one.

A solution of 21 ml 3,4-dihydro-2H-naphthalene-1-one in 200 ml glacial acetic acid was treated successively with 8.2 g dimethylamine hydrochloride and 3.0 g paraformaldehyde. The mixture was heated to 100° C. for 2 hours, the solvent was thereafter evaporated under vacuum, and the residue was taken up in 200 ml water. It was extracted three times with 100 ml portions of diethyl ether. The aqueous phase was adjusted to pH 10 by adding potassium carbonate in portions, with vigorous stirring. The product was then extracted three times with 150 ml portions of ethyl acetate. The extracts were washed with saturated sodium chloride solution and dried over sodium sulfate. After filtering, and after concentrating the filtrate by evaporation under vacuum, 15.4 g (75.6% of theoretical) of (RS)-2-dimethylaminomethyl-3,4-dihydro-2H-naphthalen-1-one remained behind as a yellowish oil.

2nd step: (1RS, 2RS)-2-dimethylaminomethyl-1-(3-methoxy-phenyl)-1,2,3,4-tetrahydro-naphth-1-ol.

A solution of 7.5 g 1-bromo-3-methoxybenzene in 15 ml of dry tetrahydrofuran was treated drop-wise, at -50° C. with stirring and under an $N_2$ protective gas atmosphere, with 25 ml of a 1.6 molar solution of n-butyllithium in n-hexane. The mixture was stirred for 30 minutes at -30° C., and a solution of 6.1 g of the product from step 1 in 120 ml of dry tetrahydrofuran was then added drop-wise. Thereafter, the mixture was stirred for 3 hours at -50° C. and for 12 hours at -20° C. After adding 100 ml hydrochloric acid (10%), the batch was extracted twice with 100 ml ethyl acetate each time. The hydrochloric acid phase was adjusted to about pH 10 by adding potassium carbonate and was extracted three times with 50 ml dichloromethane each time. The extracts were dried over sodium sulfate, the solvent was evaporated under vacuum, and the residue was purified by column chromatography, using 3/1 ethyl acetate/methanol as the elutant. 5.3 g (56.5% of theoretical) of (1RS, 2RS)-2-dimethylaminomethyl-1-(3-methoxy-phenyl)-1,2,3,4-tetrahydro-naphth-1-ol were obtained in the form of a viscous oil.

3rd step: 3-(2-dimethylaminomethyl-3,4-dihydro-naphth-1-yl)-phenol hydrochloride.

5.2 g of the product from step 2 were heated under reflux for 6 hours with 160 ml of a solution of hydrogen bromide in glacial acetic acid (33% HBr). The batch was then concentrated by evaporation under vacuum and the residue was taken up in 150 ml water. It was made alkaline with sodium carbonate and was extracted three times with 50 ml dichloromethane each time. After washing the extracts with saturated sodium chloride solution and drying them over sodium sulfate, they were concentrated by evaporation, and the residue was purified by column chromatography using 5/1 ethyl acetate/methanol as the elutant. The base of the title compound which was thus obtained was converted into the hydrochloride using trimethylchlorosilane/water in 2-butanone. Yield: 2.3 g (43.8% of theoretical). Melting point: 197–199° C.

EXAMPLE 2

Using indan-1-one, 3,4-dihydro-2H-phenanthren-1-one, 6,7,8,9-tetrahydro-benzocyclohepten-5-one, 7,8,9,10-tetrahydro-6H-benzocycloocten-5-one, 5-phenyl-3,4-dihydro-2H-naphthalen-1-one, 6-phenyl-3,4-dihydro-2H-naphthalen-1-one, 6-(3-chloro-phenyl)-3,4-dihydro-2H-naphthalen-1-one, 8,9,10,11-tetrahydro-cyclo-hepta[c]naphthalen-1-one, 3,4-dihydro-2H-anthracen-1-one or 6-(4-chloro-phenyl)-3,4-dihydro-2H-naphthalen-1-one instead of 3,4-dihydro-2H-naphthalen-1-one, and optionally other amines also, in step 1, the following compounds were obtained analogously by employing the procedure described in example 1:

2a: 3-(6-dimethylaminomethyl-8,9-dihydro-7H-benzo-cyclohepten-5-yl)-phenol hydrochloride. Melting point: 218–220° C.

2b: 3-(6-diethylaminomethyl-8,9-dihydro-7H-benzocyclohepten-5-yl)-phenol hydrochloride. Melting point: 208–211 °C.

2c: 3-(6-di-n-propylaminomethyl-8,9-dihydro-7H-benzocyclohepten-5-yl)-phenol hydrochloride. Melting point: 199–201° C.

2d: 3-{6-[(methyl-phenethyl-amino)-methyl]-8,9-dihydro-7H-benzocyclohepten-5-yl}-phenol hydrochloride. Melting point: decomposition above 117° C.

2e: 3-{6-[(benzyl-methyl-amino)-methyl]-8,9-dihydro-7H-benzocyclohepten-5-yl}-phenol hydrochloride. Melting point: decomposition above 80° C.

2f: 3-(6-dimethylaminomethyl-7,8,9,10-tetrahydrobenzocycloocten-5-yl)-phenol hydrochloride. Melting point: 251–253.5° C.

2g: 3-{6-[(cyclopropylmethyl-methyl-amino)-methyl]-8,9-dihydro-7H-benzocyclohepten-5-yl}-phenol hydrochloride. Melting point: 200–202° C.

2h: 3-(6-{[methyl-(2-pyridin-2-yl-ethyl)-amino]-methyl})-8,9-dihydro-7H-benzocyclohepten-5-yl)-phenol dihydrochloride. Melting point: 100–105° C.

2i: 3-(2-dimethylaminomethyl-3H-inden-1-yl)-phenol hydrochloride. Melting point: 210–212° C.

2j: 3-(2-dimethylaminomethyl-3,4-dihydro-phenanthren-1-yl)-phendydrochloride. Melting point: 253–254° C.

2k: 3-(2-dimethylaminomethyl-5-phenyl-3,4-dihydronaphth-1-yl)-phenol hydrochloride. Melting point: 250–253.5° C.

2l: 3-(2-dimethylaminomethyl-6-phenyl-3,4-dihydronaphth-1-yl)-phenol hydrochloride. Melting point: 242–243° C.

2m: 3-[6-(3-chloro-phenyl)-2-dimethylaminomethyl-3,4-dihydro-naphth-1-yl]-phenol hydrochloride. Melting point: decomposition above 152° C.

2n: 3-(8-dimethylaminomethyl-10,11-dihydro-9H-cyclohepta[α]naphth-7-yl)-phenol hydrochloride. Melting point: 264–267° C.

2o: 3-(2-dimethylaminomethyl-3,4-dihydro-anthracen-1-yl)-phenol hydrochloride. Melting point: 220–222° C.

2p: 3-[6-(4-chloro-phenyl)-2-dimethylaminomethyl-3,4-dihydro-naphth-1-yl]-phenol hydrochloride. Melting point: 245–247° C.

2g: 2-{6-[(furan-3-ylmethyl-amino)-methyl]-8,9-dihydro-7H-benzocyclohepten-5-yl}-phenol hydrochloride.

EXAMPLE 3

(6-methoxy-1-phenyl-3,4-dihydro-naphth-2-ylmethyl)-dimethylamine hydrochloride

1st step

A solution of 50 g 6-methoxy-3,4-dihydro-2H-naphthalen-1-one in 500 ml acetonitrile was treated with 26.6 g N,N-dimethylmethylene-immonium chloride and with two drops of acetyl chloride, and the mixture was stirred for 30 hours at 20° C. The crystalline product was isolated, washed with acetone, and dried under vacuum at 40° C. 70.9 g (92.5%) of the hydrochloride of the title compound were obtained in this manner (melting point: 180–182° C.), from which the base was released with dilute aqueous sodium hydroxide solution and was extracted with dichloromethane. After drying the extracts over sodium sulfate and evaporating the solvent under vacuum, 56.3 g (RS)-2-dimethylamino-methyl-6-methoxy-3,4-dihydro-2H-naphthalen-1-one remained behind in the form of a yellowish oil.

2nd step: (1 RS, 2 RS)-2-dimethylaminomethyl-6-methoxy-1-phenyl-1,2,3,4-tetrahydronaphth-1-ol.

A solution of 20.5 g of the product from step 1 in 300 ml of dry diethyl ether was treated drop-wise, at –60° C., while stirring and passing dry nitrogen over the batch, with 50 ml of a 2 molar solution of phenyllithium in 70/30 cyclohexane/diethyl ether. The batch was subsequently stirred for 2 hours at –60° C. and was then decomposed with 150 ml of a saturated solution of ammonium chloride. The organic phase was separated, and the aqueous phase was extracted twice with ethyl acetate. The combined organic phases were washed with saturated sodium chloride solution and dried over sodium sulfate. The oil which remained after evaporating the solvent under vacuum was purified by column chromatography using diisopropyl ether as the elutant. 21.3 g (78.0% of theoretical) of (1 RS, 2 RS)-2-dimethylaminomethyl-6-methoxy-1-phenyl-1,2,3,4-tetrahydro-naphth-1-ol were thus obtained as an oil.

3rd step: (6-methoxy-1-phenyl-3,4-dihydro-naphth-2-ylmethyl)-dimethylamine hydrochloride.

A solution of 6.3 g of the product from step 2 in 100 ml hydrochloric acid (10%) was stirred for 12 hours at 20° C. It was then made alkaline with 1 N aqueous sodium hydroxide solution and was extracted three times with dichloromethane. The extracts were washed with saturated sodium chloride solution and dried over sodium sulfate. The crude product obtained after evaporating the solvent under vacuum was purified by column chromatography using 3/1 ethyl acetate/methanol as the elutant. The base was then converted into the hydrochloride with chloro-trimethylsilane/water in 2-butanone. Yield: 5.4 g =81% of theoretical. Melting point 189–191° C.

EXAMPLE 4

(5-methoxy-1-phenyl-3,4-dihydro-naphth-2-ylmethyl)-dimethylamine hydrochloride.

The title compound was obtained in the form of white crystals, using the procedure and reaction sequence described in example 3 and using 5-methoxy-3,4-dihydro-2H-naphthalen-1-one as the starting compound. Melting point: 205–206° C.

EXAMPLE 5

5a: 6-dimethylaminomethyl-5-phenyl-7,8-dihydro-naphth-2-ol hydrochloride.

3.5 g of the product from example 3 were reacted with 100 ml of a solution of hydrogen bromide in glacial acetic acid (33% HBr), as described in example 1, step 3. After corresponding work-up, purification by column chromatography and reaction with trimethylchlorosilane/water, 2.4 g (63.7% of theoretical) of the title compound were obtained in the form of white crystals. Melting point: 189–191° C.

5b: 6-dimethylaminomethyl-5-phenyl-7,8-dihydro-naphth-1-ol hydrochloride.

The title compound was obtained analogously from the product from example 4 using the procedure described in example 5a. Melting point: 245–247° C.

EXAMPLE 6

6-dimethylaminomethyl-5-(3-hydroxy-phenyl)-7,8-dihydro-naphth-2-ol hydrochloride.

1st step: (1RS,2RS)-2-dimethylaminomethyl-6-methoxy-1-(3-methoxy-phenyl)-1,2,3,4-tetrahydro-naphth-1-ol.

The corresponding Grignard reagent was prepared by gently boiling 7.3 g magnesium turnings and 56.1 g 1-bromo-3-methoxy-benzene in 200 ml of dry tetrahydrofuran. A solution of 46.7 g (RS)-2-dimethylaminomethyl-6-methoxy-3,4-dihydro-2H-naphthalen-1-one (the product from example 3, 1st step) in 100 ml of dry tetrahydrofuran was added drop-wise thereto at +5 to +10° C. The batch was subsequently stirred for 16 hours at +22° C., and after cooling to about 10° C. was treated with 100 ml of saturated ammonium chloride solution. The reaction mixture was diluted with 100 ml water and 200 ml diethyl ether, the phases were separated and the aqueous phase was extracted twice with 100 ml portions of diethyl ether. The combined organic phases were dried over sodium sulfate and freed from the volatile constituents under vacuum. The oily residue was purified by column chromatography using ethyl acetate as the elutant, whereupon 43.9 g (64.3% of theoretical) (1RS, 2RS)-2-dimethylaminomethyl-6-methoxy-1-(3-methoxy-phenyl)-1,2,3,4-tetrahydro-naphth-1-ol were obtained.

2nd step: 6-dimethylaminomethyl-5-(3-hydroxy-phenyl)-7,8-dihydro-naphth-2-ol hydrochloride.

34.2 g of the product from step 1 were stirred with 350 ml of a solution of hydrogen bromide in glacial acetic acid (33% HBr) for 20 hours at a temperature of 100° to 110° C. The batch was then concentrated by evaporation under vacuum and the residue was taken up in 500 ml water. After work-up as described in example 1, step 2, the product was purified by column chromatography using 3/1 ethyl acetate/methanol as the elutant. The base of the title compound which was obtained in this manner was converted into the hydrochloride with trimethylchlorosilane/water in 2-butanone. Yield: 12.2 g (41.2% of theoretical). Melting point: 210–212° C.

EXAMPLE 7

Compounds 7a and 7b, which were isomeric with the product from example 6, were obtained by the procedure described in example 6, by using corresponding starting materials:
7a: 6-dimethylaminomethyl-5-(3-hydroxy-phenyl)-7,8-dihydronaphth-1-ol hydrochloride. Melting point: 260–262° C.
7b: 7-dimethylaminomethyl-8-(3-hydroxy-phenyl)-5,6-dihydronaphth-2-ol hydrochloride. Melting point: 239–242° C.

Replacement of (RS)-2-dimethylaminomethyl-6-methoxy-3,4-dihydro-2H-naphthalen-1-one in example 6, step 1, by (RS)-6-dimethylaminomethyl-2-methoxy-6,7,8,9-tetrahydro-benzocyclohepten-5-one (7c) or (RS)-2-dimethylaminomethyl-6-(3-methoxy-phenyl)- 3,4-dihydro-2H-naphthalen-1-one (7d) and further reaction using the procedure described in example 6 gave:
7c: 6-dimethylaminomethyl-5-(3-hydroxy-phenyl)-8,9-dihydro-7H-benzocyclohepten-2-ol hydrochloride. Melting point: decomposition above 110° C.
7d: 3-[2-dimethylaminomethyl-6-(3-hydroxy-phenyl)-3,4-dihydro-naphth-1 -yl]-phenol hydrochloride.

EXAMPLE 8

3-(2-dimethylaminomethyl-7-phenoxy-3,4-dihydro-naphth-1-yl)-phenol hydrochloride 1st step: 7-phenoxy-3,4-dihydro-2H-naphthalen-1-one.

A suspension of 60.8 g potassium carbonate in 300 ml of dry pyridine was treated with 35.7 g 7-hydroxy-3,4-dihydro-2H-naphthalen-1-one, and the mixture was heated to 40° C. Thereafter, 19.9 g copper(II) oxide was added thereto with stirring, followed by the drop-wise addition of 39.6 g bromobenzene. The reaction mixture was heated for 4 days under reflux. After evaporating the pyridine completely under vacuum, the residue was stirred with 200 ml ethyl acetate and was filtered through silica gel. The filtrate was washed with saturated solutions of ammonium chloride and sodium chloride, dried over sodium sulfate and concentrated by evaporation under vacuum. The residue was purified by column chromatography, using n-hexane/ethyl acetate as the elutant, whereupon 41.2 g (78.6% of theoretical) 7-phenoxy-3,4-dihydro-2H-naphthalen-1-one was obtained.

2nd step: 2-dimethylaminomethyl-7-phenoxy-3,4-dihydro-2H-naphthalen-2-one.

40.5 g of the product from step 1 in 500 ml acetonitrile were reacted, analogously to example 3, step 1, with 16.0 g N,N-dimethylmethylene-immonium chloride. After corresponding work-up, 45.8 g (91.3% of theoretical) of 2-dimethylaminomethyl-7-phenoxy-3,4-dihydro-2H-naphthalen-1-one was obtained in the form of an oil.

3rd step: (1RS, 2RS)-1-[3-(tert-butyl-diphenyl-silanoxy)-phenyl]-dimethylaminomethyl-7-phenoxy-1,2,3,4-tetrahydronaphth-1-ol.

A solution of 41.2 g (3-bromo-phenoxy)-tert-butyl-diphenyl-silane in 300 ml of dry tetrahydrofuran was treated drop-wise at –40° C., while stirring and passing dry nitrogen over the batch, with 62.5 ml of a 1.6 M solution of n-butyllithium in n-hexane. The batch was stirred for a further 30 minutes, and a solution of 25.1 g of the product from step 2 in 75 ml of dry tetrahydrofuran was then added drop-wise thereto. The reaction mixture was allowed to warm up to +20° C. over 12 hours and was decomposed by the addition of 100 ml of a saturated ammonium chloride solution. After diluting with 200 ml water and 200 ml ethyl acetate, the organic phase was separated and the aqueous phase was extracted twice with 100 ml ethyl acetate. The combined organic phases were washed with saturated sodium chloride solution, dried over sodium sulfate and concentrated by evaporation under vacuum. The residue was purified by column chromatography using ethyl acetate as the elutant, whereupon 32.9 g (61.6% of theoretical) of (1RS, 2RS)-1-[3-(tert-butyl-diphenyl-silanyloxy-phenyl]-2-dimethylaminomethyl-7-phenoxy-1,2,3,4-tetrahydro-naphth-1-ol was obtained as an almost colorless, viscous oil.

4th step: (1RS, 2RS)-2-dimethylaminomethyl-1-(3-hydroxy-phenyl)-7-phenoxy-1,2,3,4-tetrahydro-naphth-1-ol.

A solution of 31.4 g of the product from step 3 in 360 ml of dry tetrahydrofuran was treated drop-wise at +5° C. to 10° C., with stirring, with 57.5 ml of a 1 molar solution of tetra-n-butylammonium fluoride in tetrahydrofuran. After the addition was complete, the batch was stirred for 3 hours at 20° C., treated with 150 ml of a saturated solution of sodium chloride and was extracted three times with 150 ml portions of ethyl acetate. The extracts were dried over sodium sulfate and were concentrated by evaporation under vacuum. The residue was purified by column chromatography using 5/1 ethyl acetate/methanol as the elutant, whereupon 17.3 g (88.7% of theoretical) (1RS, 2RS)-2-dimethylaminomethyl-1-(3-hydroxy-phenyl)-7-phenoxy-1, 2,3,4-tetrahydro-naphth-1-ol were obtained as a viscous oil with a slight yellow coloration.

5th step: 3-(2-dimethylaminomethyl-7-phenoxy-3,4-dihydro-naphth-1-yl)-phenol hydrochloride.

15.6 g of the product from step 4 were reacted with 150 ml of 6 N hydrochloric acid as described in example 3, step 3. After an analogous work-up and conversion into the hydrochloride, 12.1 g (73.8% of theoretical) 3-(2- dimethylaminomethyl-7-phenoxy-3,4-dihydronaphth-1-yl)-phenol hydrochloride were obtained in the form of white crystals. Melting point: 210–212° C.

EXAMPLE 9

In example 8, step 2, 7-phenoxy-3,4-dihydro-2H-naphthalen-1-one was replaced by the corresponding 5-methoxy (9a), 7-phenyl (9b), 7-phenethyl (9d), 5-phenoxy (9e), 6-phenoxy (9f) and 7-n-butyl derivatives (9c) or by 2-phenoxy-6,7,8,9-tetrahydro-benzocyclohepten-5-one (9g). The following products were obtained therefrom by employing a reaction sequence and procedure analogous to example 8:

9a: 3-(2-dimethylaminomethyl-5-methoxy-3,4-dihydronaphth-1-yl)-phenol hydrochloride. Melting point: 245–247° C.
9b: 3-(2-dimethylaminomethyl-7-phenyl-3,4-dihydronaphth-1-yl)-phenol hydrochloride. Melting point: 232–233° C.
9c: 3-(7-n-butyl-2-dimethylaminomethyl-3,4-dihydronaphth-1-yl)-phenol hydrochloride. Melting point: 202–205° C.
9d: 3-(2-dimethylaminomethyl-7-phenethyl-3,4-dihydronaphth-1-yl)-phenol hydrochloride. Melting point: 233–237° C.
9e: 3-(2-dimethylaminomethyl-5-phenoxy-3,4-dihydronaphth-1-yl)-phenol hydrochloride. Melting point: 197–198° C.
9f: 3-(2-dimethylaminomethyl-6-phenoxy-3,4-dihydronaphth-1-yl)-phenol hydrochloride. Melting point: 224.5–226° C.
9g: 3-(6-dimethylaminomethyl-2-phenoxy-8,9-dihydro-7H-benzocyclohepten-5-yl)-phenol hydrochloride. Melting point: 245–247° C.

EXAMPLE 10

3-{6-[allyl-methyl-amino)-methyl]-8,9-dihydro-7H-benzocyclohepten-5-yl}-phenol hydrochloride.

1st step: 6-[(allyl-methyl-amino)-methyl]-6,7,8,9-tetrahydro-benzocyclohepten-5-one.

5.2 g 6,7,8,9-tetrahydro-benzocyclohepten-5-one, 0.96 g paraformaldehyde and 10.0 g allyl-methylamine hydrochloride in 60 ml glacial acetic acid were reacted as in example 1, step 1. After analogous work-up, 6.7 g (84.8% of theoretical) 6-[(allyl-methyl-amino)-methyl]-6,7,8,9-tetrahydro-benzocyclohepten-5-one were obtained as a yellowish oil.

Final step: 3-{6-[allyl-methyl-amino)-methyl]-8,9-dihydro-7H-benzocyclohepten-5-yl}-phenol hydrochloride.

The product from step 1 was further reacted using the procedure described in example 8, steps 3–5. 3-{6-[allyl-methyl-amino-methyl]-8,9-dihydro-7H-benzocyclohepten-5-yl}-phenol hydrochloride was thus obtained in the form of white crystals. Melting point: 156–159° C. (decomposition).

EXAMPLE 11 a) 3-[3-dimethylamino-1-(3-hydroxyphenyl)-2-methyl-propenyl]-phenol hydrochloride.

1st step: (2RS)-3-dimethylamino-1,1-bis-(3-methoxy-phenyl)-2-methyl-propan-1-ol hydrochloride.

27.0 g magnesium turnings were stirred in 150 ml of dry tetrahydrofuran. 207.6 g 1-bromo-3-methoxy-benzene, dissolved in 400 ml of dry tetrahydrofuran, were added drop-wise thereto so that the reaction mixture boiled gently. After the addition was complete, the batch was heated under reflux for a further one hour, was then cooled to +5 to 10° C., and 166.0 g (RS)-3-dimethylamino-1-(3-methoxy-phenyl)-2-methyl-propan-1-one, dissolved in 400 ml tetrahydrofuran, were added drop-wise at this temperature. The reaction mixture was allowed to stand overnight and was subsequently cooled to 5 to 10° C. again. The Griaddin solution was decomposed by adding 300 ml of 20% ammonium chloride solution. The reaction mixture was diluted with 400 ml ether, the phases were separated, and the aqueous phase was extracted twice with 250 ml ether. The combined organic phases were dried over sodium sulfate and freed from solvent. The residue (342 g) was taken up in 4000 ml 2-butanone and treated with 81.5 g trimethylchlorosilane and 13.5 ml water. 165.0 g (60% of theoretical) 3,3-bis-(2-hydroxy-phenyl-2-methyl-prop-2-enyl)-dimethylamine hydrochloride crystallized overnight at 4 to 5° C. Melting point: 158–160° C.

2nd step: 3-[3-dimethylamino-1-(3-hydroxyphenyl)-2-methyl-propenyl]-phenol hydrochloride.

58 g (2RS)-3-dimethylamino-1,1-bis-(3-methoxy-phenyl)-2-methyl-propan-1-ol hydrochloride from step 1 were dissolved in 2000 ml concentrated hydrobromic acid (47%) and heated under reflux for 7 hours. After cooling to room temperature, the reaction mixture was treated with 800 ml water, 2000 ml dichloromethane and 80 g sodium hydrogen carbonate. After separating the dichloromethane phase, the aqueous phase was extracted twice with 1000 ml ethyl acetate. The combined organic phases were dried over sodium sulfate and freed from solvent. The residue (42 g) was dissolved in a mixture consisting of 100 ml ethyl acetate and 100 ml tetrahydrofuran and was purified by column chromatography. Elution with 4/1 ethyl acetate/methanol gave 22 g base. This was dissolved in 500 ml 2-butanone and treated with 8.5 g trimethylchlorosilane and 16 ml water. The hydrochloride which crystallized out (14.6 g) was filtered out under suction and suspended in 1000 ml 2-butanone for purification. The suspension was stirred for 5 hours under reflux. After cooling to room temperature, 13.5 g hydrochloride (26.4% of theoretical) were obtained. Melting point: 222–224° C.

b) Z-3-(1-biphenyl-4-yl-3-dimethylamino-2-methyl-propenyl)-phenol hydrochloride.

The title compound was obtained in an analogous manner by the procedure described in example 11a, using (RS)-1-biphenyl-4-yl-3-dimethylamino-2-methyl-propan-1-one. Melting point: 192–194° C.

The following compounds were obtained by an analogous reaction sequence, using corresponding substituted dimethylamino-alkan-1-ones in step 1:

11c: E-3-[1-(3,4-dichloro-phenyl)-3-dimethylamino-2-methyl-propenyl]-phenol hydrochloride. Melting point: 176–178° C.
11d: Z-3-[1-(4-chloro-phenyl)-3-dimethylamino-2-methyl-propenyl]-phenol hydrochloride. Melting point: 144–146° C.
11e: Z-3-[3-dimethylamino-2-methyl-1-(4-phenoxy-phenyl)-propenyl]-phenol hydrochloride. Melting point: 190–192° C.
11f: Z-3-(3-dimethylamino-2-methyl-1-p-tolyl-propenyl)-phenol hydrochloride. Melting point: 200–201° C.
11g: Z-3-(2-dimethylaminomethyl-1-phenyl-but-1-enyl)-phenol hydrochloride. Melting point: 188–190° C.
11h: Z-3-[1-(4'-chloro-biphenyl-4-yl)-3-dimethylamino-2-methyl-propenyl]-phenol hydrochloride. Melting point: 156–158° C.

11i: Z-3-[3-dimethylamino-2-methyl-1-(4-styryl-phenyl)-propenyl]-phenol hydrochloride. Melting point: 236–237° C.

11j: Z-3-[3-dimethylamino-2-methyl-1-(4-phenethyl-phenyl)-propenyl]-phenol hydrochloride. Melting point: 183–185 0C.

11k: Z-3-[3-dimethylamino-1-(4-hydroxy-phenyl)-2-methyl-propenyl]-phenol hydrochloride.

11l: Z-3-(1-benzo[1,3]dioxol-5-yl-3-dimethylamino-2-methyl-propenyl)-phenol hydrochloride. Melting point: 121–124° C.

The delta opiate receptor binding investigations described below show that the compounds of formula (I) according to the invention are outstandingly effective as analgesics.

δ Opiate Receptor Binding Investigations

Tests to determine the affinity of the compounds of formula (I) according to the invention for the δ opiate receptor were performed on meninx homogenates (a homogenate of the brain of male Wistar rats, without the cerebellum, pons and medulla oblongata).

The rat brain, which was freshly prepared in each case, was homogenized for this purpose, while being cooled in ice, in 50 mmoles/l Tris-HCl (pH 7.4) and was centrifuged for 10 minutes at 5000 g and 4° C. After decanting and discarding the supernatant liquor, and taking up and homogenising the membrane sediment again in 50 nm moles/l Tris-HCl (pH 7.4), the homogenate was subsequently centrifuged for 20 minutes at 20,000 g and 4° C. This washing step was repeated once more. Thereafter, the supernatant liquor was decanted, the membrane sediment was homogenized in cold 50 mmoles/l Tris-HCl, 20% glycerol (w/v), 0.01% bacitracin (w/v) (pH 7.4), and was frozen in aliquots until testing was performed. For the receptor binding tests, the aliquots were thawed and diluted 1:10 with the binding test buffer.

50 mmoles/l Tris-HCl, 5 mmoles/l $MgCl_2$ (pH 7.4) supplemented with 0.1% (w/v) bovine serum albumin, with 1 nmole/l ($^3$H)-2-D-ala-deltorphin II as the radioactive ligand, was used as the buffer in the binding test. The proportion of non-specific binding was determined in the presence of 10 μmoles/l naloxone.

In further batches, the compounds according to the invention were added in a series of concentrations and the displacement of the radioactive ligand from its specific binding was determined. The respective triple batches were incubated for 90 minutes at 37° C. and were subsequently harvested by means of filtration through glass fiber filters (GF/B) for the determination of the radioactive ligand bound to the membrane homogenate. The radioactivity of the glass fiber filter discs was measured in a β-counter after adding a scintillator.

The affinity of the compounds according to the invention for the δ opiate receptor was calculated by the mass action law, by means of non-linear regression, as the $IC_{50}$ value. $K_i$ values were calculated from the $IC_{50}$ values using the Cheng-Prussoff equation. The $K_i$ values are given as mean values ± standard deviations of ≧3 tests which were independent of each other.

TABLE 1

| Example No. | δ opiate receptor binding $K_i$ (nmoles/I) | | |
|---|---|---|---|
| 1 | 55.8 | ± | 4.6 |
| 2a | 17.2 | ± | 4.3 |
| 2b | 728.0 | ± | 146.0 |
| 2c | 294.0 | ± | 106.0 |
| 2d | 54.3 | ± | 8.2 |
| 2e | 936.0 | ± | 32.0 |
| 2f | 46.3 | ± | 10.1 |
| 2g | 182.0 | ± | 12.0 |
| 2h | 223.0 | ± | 86.0 |
| 2i | 157.0 | ± | 16.0 |
| 2j | 80.8 | ± | 29.7 |
| 3 | 456.0 | ± | 62.0 |
| 4 | 517.0 | ± | 45.0 |
| 5 | 843.0 | ± | 23.0 |
| 6 | 40.9 | ± | 6.7 |
| 7 | 21.6 | ± | 6.2 |
| 8 | 25.7 | ± | 10.2 |
| 9a | 23.9 | ± | 0.9 |
| 9b | 39.3 | ± | 2.2 |
| 9c | 42.2 | ± | 16.0 |
| 10 | 679.0 | ± | 214.0 |
| 11a | 34.0 | ± | 5.8 |
| 11b | 23.7 | ± | 1.7 |

Table 1 shows that the amino compounds according to the invention are effective as analgesics, wherein this biological efficacy is partially or predominantly imparted via δ opiate receptors and is detected thereby.

As effective and selective δ opioid agonists and -antagonists, the compounds of general formula (I) according to the invention can be used as agents for pathological conditions which are usually treated with agonists and antagonists of the δ opioid receptor. The compounds of general formula I can preferably be used as analgesics.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A substituted amino compound corresponding to formula I:

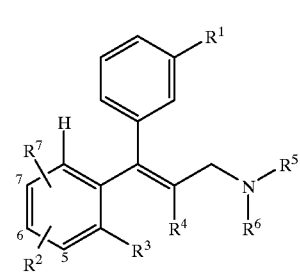

(I)

wherein $R^1$ represents OH or O—$C_{3-7}$-cycloalkyl;

$R^2$ represents H, OH, $C_{1-6}$-alkyl, O—$C_{3-7}$-cycloalkyl, O-aryl, $C_{2-6}$-alkenyl-aryl, Cl, F, $CF_3$, $C_{1-6}$-alkoxy, aryl, heterocyclyl, $C_{1-6}$-alkyl-heterocyclyl, $C_{1-6}$-alkyl-aryl, or 5,6- or 6,7-benzo which is unsubstituted or mono- or di-substituted with Cl, F, $CF_3$, $C_{1-6}$-alkyl, O—$C_{1-6}$-alkyl or OH; or $R^2$ and $R^7$ together represent —O—$(CH_2)_{(1-2)}$—O— in the 5,6- or 6,7-position;

$R^3$ represents H;

R⁴ represents C$_{1-6}$-alkyl, or

R³ and R⁴ together represent —(CH$_2$)$_{(1-4)}$—;

R⁵ represents C$_{1-6}$-alkyl or C$_{3-7}$-cycloalkyl;

R⁶ represents C$_{1-6}$-alkyl, C$_{1-6}$-alkyl-aryl, C$_{1-6}$-alkyl-heterocyclyl, —CH$_2$—CH=C(R⁸)$_2$, —CH$_2$—(C$_{3-7}$)-cycloalkyl or C$_{3-7}$-cycloalkyl;

R⁷ represents H, OH, C$_{1-6}$-alkyl, O—C$_{3-7}$-cycloalkyl, O-aryl, C$_{2-6}$-alkenyl-aryl, C$_{1-6}$-alkoxy, Cl, F, CF$_3$, aryl, heterocyclyl, C$_{1-6}$-alkyl-heterocyclyl, C$_{1-6}$-alkyl-aryl, or 5,6- or 6,7-benzo which is unsubstituted or mono- or di-substituted with Cl, F, CF$_3$, C$_{1-6}$-alkyl, O—C$_{1-6}$-alkyl or OH; and R⁸ represents H or CH$_3$;

or a pharmaceutically acceptable salt thereof.

2. A substituted amino compound according to claim 1, wherein R², R⁶ and R⁷ represent C$_{1-6}$-alkyl-heterocyclyl or C$_{1-6}$-alkyl-aryl.

3. A substituted amino compound according to claim 1, wherein R² and R⁷ represent aryl or heterocyclyl.

4. A substituted amino compound according to claim 1, wherein R¹ represents OH, R⁵ represents C$_{1-6}$-alkyl, and R⁶ represents C$_{1-6}$-alkyl.

5. A substituted amino compound according to claim 1, wherein R¹ represents OH, R⁵ represents methyl, and R represents methyl.

6. A pharmaceutical composition comprising a substituted amino compound according to claim 1, and at least one pharmaceutically acceptable carrier or adjuvant.

7. A pharmaceutical composition according to claim 6, wherein said substituted amino compound is an analgesic, and said composition comprises an analgesically effective amount of said substituted amino compound.

8. An amino compound according to claim 1, wherein said heterocyclyl is a 5- or 6- membered ring that contains at least one heteroatom selected from the group consisting of nitrogen, oxygen and sulfur.

9. An amino compound according to claim 8, wherein said heterocyclyl is selected from the group consisting of 1,4-dioxane, tetrahydrofuran, 1-4-thioxane, furane, thiophene, pyridine, pyrimidine, thiazole, oxazole, isooxazole, pyridazine, pyrazine, quinoline, isoquinoline, phthalazine and quinazoline.

10. A substituted amino compound corresponding to formula I:

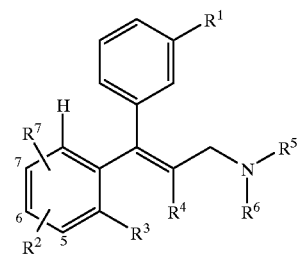

(I)

wherein

R¹ represents H, OH, O—C$_{1-6}$-alkyl or O—C$_{3-7}$-cycloalkyl;

R² represents OH, O—C$_{3-7}$-cycloalkyl, O-aryl, C$_{2-6}$-alkenyl-aryl, aryl, heterocyclyl, C$_{1-6}$-alkyl-heterocyclyl, C$_{1-6}$-alkyl-aryl, or 5,6- or 6,7-benzo which is unsubstituted or mono- or di-substituted with Cl, F, CF$_3$, C$_{1-6}$-alkyl, O—C$_{1-6}$-alkyl or OH; or R² and R⁷ together represent —O—(CH$_2$)$_{(1-2)}$—O— in the 5,6- or 6,7-position;

R³ represents H;

R⁴ represents C$_{1-6}$-alkyl, or

R³ and R⁴ together represent —(CH$_2$)$_{(1-4)}$—;

R⁵ represents C$_{1-6}$-alkyl or C$_{3-7}$-cycloalkyl;

R⁶ represents C$_{1-6}$-alkyl, C$_{1-6}$-alkyl-aryl, C$_{1-6}$-alkyl-heterocyclyl, —CH$_2$—CH=C(R⁸)$_2$, —CH$_2$—(C$_{3-7}$)-cycloalkyl or C$_{3-7}$-cycloalkyl;

R⁷ represents H, OH, C$_{1-6}$-alkyl, O—C$_{3-7}$-cycloalkyl, O-aryl, C$_{2-6}$-alkenyl-aryl, C$_{1-6}$-alkoxy, Cl, F, CF$_3$, aryl, heterocyclyl, C$_{1-6}$-alkyl-heterocyclyl, C$_{1-6}$-alkyl-aryl, or 5,6- or 6,7-benzo which is unsubstituted or mono- or di-substituted with Cl, F, CF$_3$, C$_{1-6}$-alkyl, O—C$_{1-6}$-alkyl or OH; and R⁸ represents H or CH$_3$;

or a pharmaceutically acceptable salt thereof.

11. A substituted amino compound according to claim 10, wherein R², R⁶ and R⁷ represent C$_{1-6}$-alkyl-heterocyclyl or C$_{1-6}$-alkyl-aryl.

12. A substituted amino compound according to claim 10, wherein R² and R⁷ represent aryl or heterocyclyl.

13. A substituted amino compound according to claim 10, wherein R¹ represents OH or —O—C$_{1-6}$-alkyl, R⁵ represents C$_{1-6}$-alkyl, and R⁶ represents C$_{1-6}$-alkyl.

14. A substituted amino compound according to claim 10, wherein R¹ represents OH, R⁵ represents methyl, and R⁶ represents methyl.

* * * * *